United States Patent [19]

Rowsell et al.

[11] 4,070,496

[45] Jan. 24, 1978

[54] PHOSPHINE OXIDES HAVING A PHYSIOLOGICAL COOLING EFFECT

[75] Inventors: David G. Rowsell, Staines; David J. Spring, Datchet, both of England

[73] Assignee: Wilkinson Sword Limited, London, England

[21] Appl. No.: 397,374

[22] Filed: Sept. 14, 1973

[30] Foreign Application Priority Data

Sept. 27, 1972  United Kingdom ............... 44622/72

[51] Int. Cl.$^2$ ..................... A61K 31/66; A61K 7/16
[52] U.S. Cl. ......................... 424/45; 131/120; 132/89; 252/32.5; 252/522; 424/49; 424/57; 424/65; 424/70; 424/73; 424/148; 424/156; 424/168; 424/198; 424/230; 424/329; 424/358; 426/3; 426/590
[58] Field of Search ................ 424/198, 45; 260/606.5 P

[56] References Cited

U.S. PATENT DOCUMENTS

| | | | |
|---|---|---|---|
| 3,158,461 | 11/1964 | Weil | 71/93 |
| 3,304,263 | 2/1967 | Yoke et al. | 260/606.5 |
| 3,326,768 | 6/1967 | MacMillan | 424/265 |
| 3,331,878 | 7/1967 | Priestley | 260/606.5 |
| 3,338,701 | 5/1974 | Weil | 71/71 |
| 3,644,653 | 2/1972 | Tcheiltcheff | 424/358 |

FOREIGN PATENT DOCUMENTS 976,974  12/1964  United Kingdom ............. 260/606.5

OTHER PUBLICATIONS

Chemical Abstracts, 7th Collective Index, (1962-1966), vols. 56-65, pp. 13780s-13782s.
Chemical Abstracts, 8th Collective Index, (1967-1971), vols. 66-75, pp. 18623s-18627s.
Wilson et al., Textbook of Organic Medicinal and Pharmaceutical Chemistry, 4th Edition, (1962), pp. 111-112.
Remington's Pharmaceutical Sciences, 13th Edition, (1965), p. 855.

*Primary Examiner*—Leonard Schenkman
*Attorney, Agent, or Firm*—Leydig, Voit, Osann, Mayer & Holt, Ltd.

[57] ABSTRACT

Compounds and compositions are disclosed having a physiological cooling action on the skin. The compositions contain as the active ingredient certain phosphine oxides. The compositions disclosed include toilet and cosmetic preparations, e.g. toilet water, after-shave lotions, soaps, cosmetic creams and lotions, dentifrices and cleansing tissues, and tobacco and tobacco preparations.

10 Claims, No Drawings

PHOSPHINE OXIDES HAVING A PHYSIOLOGICAL COOLING EFFECT

FIELD OF THE INVENTION

This invention relates to topical and other compositions having a physiological cooling effect on the skin and on the mucous membranes of the body, particularly the nose, mouth, throat and gastrointestinal tract.

BACKGROUND OF THE INVENTION

Menthol is well known for its physiological cooling effect on the skin and mucous membranes of the mouth and has been extensively used as a flavouring agent (menthol being a major constituent of oil of peppermint) in foodstuffs, beverages, dentifrices, mouthwashes, etc. and as a component in a wide range of toiletries, liniments and lotions for topical application. Menthol is also a well known tobacco additive for producing a "cool" sensation in the mouth when smoking.

It is well established that the "cooling" effect of menthol is a physiological effect due to the direct action of menthol on the nerve endings of the human body responsible for the detection of hot or cold and is not due to latent heat of evaporation. It is believed that the menthol acts as a direct stimulus on the cold receptors at the nerve endings which in turn stimulate the central nervous system.

Although menthol is well established as a physiological coolant its use, in some compositions, is circumscribed by its strong minty odour and its relative volatility.

Other compounds have been mentioned in the art as having a physiological cooling effect e.g. 2,4,6-trimethyl-4-heptanol (Parfums-Cosmetiques-Savons, May 1956, pages 17-20) and N,N-diethyl--ethylbutanamide (French Pat. No. 1,572,332).

OBJECTS OF INVENTION

The object of the present invention is to provide other compounds having a physiological cooling effects similar to that obtained with menthol but without its attendant disadvantages.

It is a further object of the invention to provide ingestible, topical and other compositions containing such compounds in an amount to provide a physiological cooling effect when such compositions are used in or by the human body.

It is a further object to provide a method of stimulating the cold receptors of the body using agents other than menthol.

SUMMARY OF INVENTION

According to the invention we have found a group of phosphine oxides which are capable of stimulating the cold receptors of the nervous system of the body.

DETAILED DESCRIPTION OF INVENTION

The compounds having this physiological cooling effect and usable according to this invention are phosphine oxides of the formula:

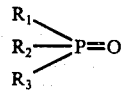

where $R_1$ is an alkyl radical containing at least 3 carbon atoms, $R_2$ is an alkyl radical containing at least 3 carbon atoms or a cycloalkyl radical and $R_3$ is an alkyl or cycloalkyl radical, $R_1$, $R_2$ and $R_3$ together presenting a total of from 13-17 carbon atoms, and at least one of $R_1$, $R_2$ and $R_3$ having branching in an $\alpha$, $\beta$ or $\gamma$ position relative to the phosphorus atom. For the avoidance of doubt, branching in this context is to be taken to include cyclic structures, as well as branched chain acyclic groups, i.e. this condition will be met by compounds in which either of $R_2$ and $R_3$ is cycloalkyl, the carbon atom of $R_2$ or $R_3$, as the case may be, in the $\alpha$-position relative to the phosphorus atom being part of the ring and therefore being considered as "branched". Preferably $R_1$, $R_2$ and $R_3$ are such that any two, when taken together present a total of at least 6 carbon atoms. Compounds of highest activity and especially preferred in accordance with this invention are those where $R_1$ is a straight chain alkyl group of from 4-8 carbon atoms, more especially 5-8 carbon atoms, $R_2$ is a branched chain alkyl group of from 3-5 carbon atoms, and especially isopropyl, sec.-butyl, isobutyl or isopentyl, and $R_3$ is an alkyl group, preferably a branched chain alkyl group, of from 3-6 carbon atoms, preferably 4 or 5 carbon atoms, or a cyclopentyl group, $R_1$, $R_2$ and $R_3$ providing a total of from 13-16 carbon atoms.

Generally speaking, therefore, the present invention provides compositions, in particular ingestible compositions and compositions for topical application, capable of stimulating the cold receptors of the nervous system of the human body comprising an effective amount of a cold receptor stimulant and a carrier therefor, the stimulant comprising one or more of the above defined phosphine oxides.

The phosphine oxides used in this invention may be readily prepared by conventional routes. If two alkyl groups are the same, then dialkylphosphinyl chlorides, $R_2POCl$, may be prepared by the action of thionyl chloride on tetraalkyldiphosphine disulphides, or preferably by the action of chloride on secondary phosphine oxides (prepared from Grignard reagents and diethyl phosphite). These dialkylphosphinyl chlorides will react with Grignard reagents to form the desired tertiary phosphine oxides.

If all three alkyl groups of a tertiary phosphine oxide are different then the following route is satisfactory. Reaction between a Grignard reagent, RMGX, and diethyl chlorphosphite gives ethyl alkylphosphinite. This latter compound, when allowed to react with a Grignard reagent, R'MgX, will give the unsymmetrical secondary phosphine oxide, RR'P(O)H. Tertiary phosphine oxides can be prepared from these secondary phosphine oxides as described previously.

Many of these reactions are described in Organic Phosphorus Compounds, Volumes 3 and 4, edited by G. M. Kosolapoff and L. Maier, published by Wiley-Interscience, 1972.

Many of the compounds used in this invention are capable of existing optical isomers and, depending on the starting materials and the methods used, the compounds of this invention may be isomerically pure, i.e. consisting of one optical isomer, or they may be isomeric mixtures. Generally speaking the compounds will be used as a mixture of optical isomers, but in some cases the degree of cooling produced by the compounds will differ as between isomers, in which case one or other isomer will be preferred.

Typical phosphine oxides suitable for use in accordance with the present invention and prepared by the above described general techniques are tabulated in the Table. Also included is an indication of the strength of the cooling effect imparted to the skin by these compounds. This was assessed by a panel of observers who were asked to assess the cooling effect produced by each compound and give the cooling effect a rating on an arbitrary scale. The results are given in the Table, the more stars the greater the cooling effect.

ments, oils and ointments applied to the external surfaces of the human body, whether for medical or other reasons, but also compositions applied to, or which in normal usage, come in contact with, internal mucous membranes of the body, such as those of the nose, mouth, or throat, whether by direct or indirect application or inhalation, and thus include nasal and throat sprays, dentifrice, mouthwash and gargle compositions.

| $R_1$ | $R_2$ | $R_3$ | Boiling Point ° C/mm Hg | Activity |
|---|---|---|---|---|
| n-$C_7H_{15}$- | iso-$C_4H_9$ | sec-$C_4H_9$ | 123–5/.004 | ***** |
| n-$C_7H_{15}$- | iso-$C_3H_7$ | sec-$C_4H_9$ | 115–20/.07 | ***** |
| n-$C_8H_{17}$ | iso-$C_3H_7$ | sec-$C_4H_9$ | 125–30/.015 | ***** |
| n-$C_8H_{17}$ | iso-$C_4H_9$ | sec-$C_4H_9$ | 130–5/.02 | **** |
| n-$C_6H_{13}$ | iso-$C_4H_9$ | sec-$C_4H_9$ | 119–21/.01 | **** |
| n-$C_8H_{17}$ | sec-$C_4H_9$ | sec-$C_4H_9$ | 117/.06/ | **** |
| n-$C_6H_{13}$ | iso-$C_3H_7$ | sec-$C_4H_9$ | 107–110/.02 | **** |
| n-$C_6H_{13}$ | iso-$C_3H_7$ | cyclo-$C_5H_9$ | 128–30/.01 | **** |
| n-$C_7H_{15}$ | n-$C_4H_9$ | (n-$C_3H_7$)($CH_2$)CH | 133/.03 | **** |
| n-$C_7H_{15}$ | iso-$C_4H_9$ | cyclo-$C_5H_9$ | 132–8/.01 | **** |
| n-$C_7H_{15}$ | iso-$C_3H_7$ | cyclo-$C_5H_9$ | 135–40/.02 | **** |
| n-$C_6H_{13}$ | iso-$C_3H_7$ | iso-$C_5H_{11}$ | 118–20/.01 | **** |
| n-$C_6H_{13}$ | iso-$C_4H_9$ | iso-$C_5H_{11}$ | 115/.03 | **** |
| n-$C_6H_{13}$ | t-$C_4H_9$ | iso-$C_5H_{11}$ | 112–4/.02 | **** |
| n-$C_7H_{15}$ | iso-$C_3H_7$ | iso-$C_5H_{11}$ | 120–25/.015 | *** |
| n-$C_5H_{11}$ | sec-$C_4H_9$ | iso-$C_4H_9$ | 110–16/.001 | *** |
| n-$C_6H_{13}$ | sec-$C_4H_9$ | sec-$C_4H_9$ | 98/.05 | *** |
| n-$C_5H_{11}$ | sec-$C_4H_9$ | sec-$C_4H_9$ | 86/.06 | *** |
| n-$C_7H_{15}$ | iso-$C_4H_9$ | iso-$C_4H_9$ | 120/2.03 | *** |
| n-$C_6H_{13}$ | iso-$C_4H_9$ | iso-$C_4H_9$ | 109–11/.03 | *** |
| n-$C_7H_{15}$ | n-$C_4H_9$ | (n-$C_3H_7$)($CH_3$)CH | 133/0.03 | *** |
| n-$C_7H_{15}$ | sec-$C_4H_9$ | sec-$C_4H_9$ | 124/.02 | *** |
| n-$C_5H_{11}$ | t-$C_4H_9$ | n-$C_5H_{11}$ | 128/.01 | *** |
| n-$C_5H_{11}$ | iso-$C_5H_{11}$ | iso-$C_5H_{11}$ | 133–5/.2 | *** |
| n-$C_6H_{13}$ | iso-$C_5H_{11}$ | iso-$C_5H_{11}$ | 137–91.15 | *** |
| n-$C_6H_{13}$ | iso-$C_3H_7$ | n-$C_6H_{13}$ | 124/.03 | *** |
| n-$C_6H_{13}$ | t-$C_4H_9$ | n-$C_6H_{13}$ | 126–8/.005 | *** |
| n-$C_6H_{13}$ | t-$C_4H_9$ | n-$C_4H_9$ | 112–4/.02 | *** |
| n-$C_5H_{11}$ | iso-$C_5H_{11}$ | i-$C_4H_9$ | 107/.02 | *** |
| n-$C_8H_{17}$ | iso-$C_3H_7$ | cyclo-$C_5H_9$ | 150–2/.03 | *** |
| n-$C_5H_{11}$ | iso-$C_4H_9$ | cyclo-$C_5H_9$ | 126–8/.03 | *** |
| n-$C_6H_{13}$ | iso-$C_5H_{11}$ | sec-$C_4H_9$ | 93–5/.01 | *** |
| n-$C_6H_{13}$ | iso-$C_4H_9$ | cyclo-$C_5H_9$ | 122–5/.03 | *** |
| n-$C_6H_{13}$ | iso-$C_4H_9$ | n-$C_6H_{13}$ | 120/.02 | *** |
| n-$C_6H_{13}$ | t-$C_4H_9$ | n-$C_3H_7$ | 95–7/.01 | *** |
| n-$C_4H_9$ | t-$C_4H_9$ | iso-$C_5H_{11}$ | 107–8/.03 | *** |
| iso-$C_5H_{11}$ | iso-$C_5H_{11}$ | iso-$C_5H_{11}$ | 125–6/.04 | *** |
| iso-$C_4H_9$ | iso-$C_5H_{11}$ | cyclo-$C_5H_9$ | 120–2/.015 | ** |
| sec-$C_4H_9$ | iso-$C_5H_{11}$ | sec-$C_4H_9$ | 89/.09 | ** |
| iso-$C_4H_9$ | iso-$C_4H_9$ | ($C_2H_5$)$_2$$CHCH_2$ | 106/.05 | ** |
| iso-$C_5H_{11}$ | iso-$C_5H_{11}$ | iso-$C_4H_9$ | 114–5/.15 | ** |
| iso-$C_5H_{11}$ | iso-$C_5H_{11}$ | t-$C_4H_9$ | 105–8/.01 | ** |
| ($C_2H_5$)($CH_3$)$CHCH_2$ | ($C_2H_5$)($CH_3$)$CHCH_2$ | t-$C_4H_9$ | 101–3/.01 | ** |
| n-$C_4H_9$ | n-$C_4H_9$ | cyclo-$C_7H_{13}$ | 126/.04 | ** |
| iso-$C_4H_9$ | iso-$C_4H_9$ | cyclo-$C_6H_{11}$ | 115/.03 | ** |
| iso-$C_4H_9$ | iso-$C_4H_9$ | (n-$C_6H_{13}$)($CH_3$)CH | 110–1/.01 | ** |
| iso-$C_3H_7$ | n-$C_4H_9$ | (n-$C_4H_9$)($C_2H_5$)$CHCH_2$ | 110–1/.03 | ** |
| iso-$C_5H_{11}$ | iso-$C_5H_{11}$ | sec-$C_4H_9$ | 107–9/.03 | ** |
| n-$C_5H_{11}$ | cyclo-$C_5H_9$ | cyclo-$C_5H_9$ | 152–51.03 | ** |
| n-$C_4H_9$ | iso-$C_4H_9$ | (n-$C_4H_9$)($C_2H_5$)CH | 95–6/.01 | * |
| iso-$C_4H_9$ | iso-$C_4H_9$ | ($C_2H_5$)($CH_3$)$CHCH_2$ | 90/.05 | * |
| ($C_2H_5$)($CH_3$)$CHCH_2$ | ($C_2H_5$)($CH_3$)$CHCH_2$ | ($C_2H_5$)($CH_3$)$CHCH_2$ | 100–5/.04 | * |
| n-$C_3H_7$ | n-$C_3H_7$ | p-menth-3-yl | 115–20/.03 | * |
| iso-$C_4H_9$ | iso-$C_4H_9$ | n-$C_9H_{19}$ | 129–32/.01 | * |

The compounds of this invention find utility as additives for a wide variety of compositions for consumption by or application to the human body, i.e., as additives for consumer products which are prepared for a human body use. Broadly speaking, these compositions can be divided into comestible and topical compositions, both terms being taken in their broadest possible sense. Thus comestible is to be taken as including not only foodstuffs and beverages taken into the mouth and swallowed, but also other orally ingested compositions taken for reasons other than their nutritional value, e.g. indigestion tablets, antacid preparations, laxatives etc. Comestible compositions are also to be taken to include edible compositions taken by mouth, but not necessarily swallowed, e.g. chewing gum. Topical compositions are to be taken as including not only compositions such as perfumes, powders and other toiletries, lotions, liniments, oils and ointments applied to the external surfaces of the human body, whether for medical or other reasons, but also compositions applied to, or which in normal usage, come in contact with, internal mucous membranes of the body, such as those of the nose, mouth, or throat, whether by direct or indirect application or inhalation, and thus include nasal and throat sprays, dentifrice, mouthwash and gargle compositions. Topical compositions is also to be taken to include toilet articles such as cleansing tissues and toothpicks.

A further class of compositions included within the scope of this invention are tobacco and associated articles e.g. pipe and cigarette fillers, especially filter tips for cigarettes.

The compositions of this invention will contain an amount of the phosphine oxide sufficient to stimulate the cold receptors in the areas of the skin or mucous membrane with which the compositions come into contact and thereby promote the desired cold sensation. The degree and longevity of cooling sensation varies from compound to compound and therefore the quantity of stimulant used in each composition will vary widely. As a guide, it may be said that, with the more active compounds of the invention, a significant cooling sensation is achieved upon application to the skin of as little as 0.05 ml of a 0.1 weight percent solution of the active ingredient in ethanol. For the less active compounds a significant cooling effect is achieved only with more concentrated solutions, e.g. containing 5.0% by weight or more of the active ingredient.

In formulating the compositions of this invention the phosphine oxide will usually be incorporated into a carrier which may be completely inert or which may be or contain other active ingredients. A wide variety of carriers will be suitable, depending upon the end use of the composition, such carriers including solids, liquids, emulsions, foams and gels. Typical carriers for the phosphine oxides include aqueous or alcoholic solutions; oils and fats such as hydrocarbon oils, fatty acid esters, long chain alcohols and silicone oils; finely divided solids such as starch or talc; cellulosic materials such as paper tissue; tobacco; low-boiling hydrocarbons and holohydrocarbons used as aerosol propellants; gums and natural or synthetic resins.

In most compositions according to the invention the carrier will be or contain as an adjuvant one or more of the following: an antacid, antiseptic or analgesic, a flavourant, colourant, or odourant, or a surfactant.

The following illustrate the range of compositions into which the compounds of this invention can be incorporated:

1. Edible or potable compositions including alcoholic and non-alcoholic beverages, confectionery, chewing gum; cachous; ice cream; jellies;
2. Toiletries including after shave lotions, shaving soaps, creams and foams, toilet water, deodorants and antiperspirants, "solid colognes", toilet soaps, bath oils and salts, shampoos, hair oils, talcum powders, face creams, hand creams, sunburn lotions, cleansing tissues, dentifrices, toothpicks, mouthwashes, hair tonics, eyedrops.
3. Medicaments including antiseptic ointments, pile ointments, liniments, lotions, decongestants, counter-irritants, cough mixtures, throat lozenges, antacid and indigestion preparations, oral analgesics;
4. Tobacco preparations including cigars, cigarettes, pipe tobacco, chewing tobacco and snuff, tobacco filters, especially filter tips for cigarettes.
5. Miscellaneous compositions such as water soluble adhesive compositions for envelopes, postage stamps, adhesive labels etc.

Particular preparations according to the invention are discussed in more detail below.

Edible and Potable Compositions

The edible and potable compositions of this invention will contain the active cooling compound in combination with an edible carrier and usually a flavouring or colouring agent. The particular effect of the compounds of the invention is to create a cool of fresh sensation in the mouth, and in some cases, even in the stomach, and therefore they find particular utility in sugar-based confectionery such chocolate, boiled sweets, mints and candy, in ice cream and jellies and in chewing gum. The formulation of such confections will be by ordinary techniques and according to conventional recipes and as forms no part of this invention. The active compound will be added to the receipe at a convenient point and in amount sufficient to produce the desired cooling effect in the final product. As already indicated, the amount will vary depending upon the particular compound, the degree of cooling effect desired and the strength of other flavourants in the recipe. For general guidance, however, amounts in the range 0.01 to 5.0% by weight based on the total compositions will be found suitable.

Similar considerations apply to the formulation of beverages. Generally speaking the compounds will find most utility in soft drinks e.g. fruit squashes, lemonade, cola etc., but may also be used in alcoholic beverages. The amount of compound used will generally be in the range 0.005 to 2.5% by weight based on the total composition.

Toiletries

Because of the cooling sensation imparted to the skin, a major utility of the compounds of this invention will be in a wide range of toilet preparations and toilet articles. The particular preparations discussed below are to be taken as exemplary.

A major utility will be in after shave lotions, toilet water etc., where the compound will be used in alcoholic or aqueous alcoholic solution, such solutions usually also containing a perfume or mild antiseptic or both. The amount of phosphine oxide added to the formulation will usually be in the range 0.1 to 3.0% by weight based on the total composition.

Another field of utility will be in soaps, shampoos, bath oils etc. where the compounds will be used in combination with an oil or fat or a natural or synthetic surfactant e.g. a fatty acid salt or a lauroylsulphate salt, the composition usually also contaning an essential oil or perfume. The range of soap compositions will include soaps of all kinds e.g. toilet soaps, shaving soaps, shaving foams etc. Usually the active compound will be added to the formulation in amount of from 0.5 to 4.0% by weight.

A further class of toilet compositions into which the compounds of this invention may be incorporated includes cosmetic creams and emollients, such creams and emollients usually comprising a base emulsion and optionally a range of ingredients such as wax, preservative, perfume, antiseptics, astringents, pigments etc. Also included within this class are lipstick compositions such compositions usually comprising an oil and wax base into which the compound can be incorporated along with the conventional ingredients i.e. pigments, perfumes etc. Once again the formulation of such compositions, apart from the incorporation of the active compound, usually in an amount of from 0.01 to 5.0% by weight, is conventional.

Compositions for oral hygiene containing the cold receptor stimulants of this invention include mouthwash, gargle and dentifrice compositions. The first two may be considered together and will usually comprise an aqueous, alcoholic or aqueous-alcoholic solution of an antiseptic often coloured or flavoured for palatability, to which the compound is added in an amount of from 0.01 to 0.5% by weight.

Dentifrice compositions may be of the solid block, powder, paste or liquid type and will usually comprise a finely divided abrasive or polishing material, e.g. precipitated chalk, silica, magnesium silicate, aluminium hydroxide or other similar materials well known in the art, and a detergent or foaming agent. Optional ingredients which may also be included are flavouring agents and colourants, antiseptics, lubricants, thickeners, emulsifiers or plasticizers. The amount of active compound added in such compositions will generally be from 0.01 to 1.0% by weight based on the total composition.

Medicaments

Because of their cooling effect on the skin and on the mucous membranes of the mouth, throat and nose and of the gastrointestinal tract the compounds of this invention may be used in a variety of oral medicines, nasal and throat sprays, and topical compositions, particularly where a counter-irritant is required. In particular the compounds of the invention may be formulated into antacid and indigestion remedies, in particular those based on sodium bicarbonate, magnesium oxide, calcium or magnesium carbonate, aluminium or magnesium hydroxide or magnesium trisilicate. In such compositions the compounds will usually be added in an amount of from 0.01 to 0.5% by weight.

The compounds of the invention may also be included in oral analgesic compositions e.g. with acetylsalicylic acid or its salts, and in nasal decongestants e.g. those containing ephedrine.

Tobacco Preparations

The compounds of this invention may be incorporated directly into tobacco, e.g. in the form of pipe tobacco, cigars, cigarettes, snuff or chewing tobacco, to give a cool effect when smoking but without the attendant strong and characteristic odour which is associated with mentholated tobacco and cigarettes. Such compositions also have considerable storage stability, which is in contrast with mentholated products. However, a more advantageous utilisation of the compounds of this invention is in pipe or cigarette filters, in particular, filter tipped cigarettes. The pad of filter material, which may be of any of the well known types, e.g. cellulose acetate, paper, cotton α-cellulose or asbestos fiber, is simply impregnated with an alcoholic solution of the phosphine oxide and dried to deposit the compound in the filter pad. The effect is to give a pleasant cool sensation in the mouth when the cigarette is smoked. As little as 0.003 mg. of the compound is effective.

The following preparative Examples A and B are given to illustrate the general procedures for the preparation of phosphine oxides used in the compositions of this invention, Example A illustrating the general procedure suitable for compounds where at least two of $R_1$, $R_2$ and $R_3$ are the same, and Example B illustrating the general procedure where $R_1$, $R_2$ and $R_3$ are all different. All temperatures are given in degrees Centigrade.

PREPARATIVE EXAMPLE A

Preparation Of Diisobutyl-n-heptylphosphine Oxide

A solution of di-isobutylphosphinyl chloride* (3.9g., 0.02 mole) in tetrahydrofuran (50 ml.) was added dropwise to a refluxing solution of n-heptylmagnesium bromide (prepared from magnesium turnings (1.2g., 0.05 mole), n-heptyl bromide (9.0g., 0.05 mole) and tetrahydrofuran (100 ml.)). The mixture was heated under reflux for 18 hours. After cooling to room temperature, the reaction mixture was poured onto ice and 2N HCl (300 ml.), and extracted with methylene dichloride (4 × 200 ml.). The combined extracts were washed with lithium hypochlorite solution, 2N NaOH solution and finally with water, then dried ($MgSO_4$). The solvent was removed by distillation and the residual yellow oil (8g.) was eluted with chloroform down a silica gel column. The product ($R_f$ = 0.1–0.2 on silica t.l.c. ($CHCl_3$)) was finally distilled to yield diisobutyl-n-heptyl-phosphine oxide as a colourless liquid, bp. 120°–2°/0.03 mm. (Found C 68.8; H 13.0; $C_{15}H_{33}OP$ requires C 69.3; H, 12.7%.

* Diisobutylphosphinyl chloride was prepared by chlorinating diisobutylphosphine oxide (from isobutylmagnesium bromide and diethyl phosphite) with chlorine, see eg. R. H. Williams, L. A. Hamilton J. Am. Chem. Soc. (1952), 74, 5418.

Symmetrical dialkylphosphinyl chlorides can also be made by the routes described by P. J. Christen, L. M. van der Linde, Receuil (1959), 78, 543 and K. A. Pollart, M. J. Harwood, J. Org. Chem. (1962), 27, 4444.

PREPARATIVE EXAMPLE B

Preparation of Iso-butyl-sec-butyl n-heptyl phosphine oxide

Part A

A solution of sec-butyl magnesium bromide (prepared from magnesium 12g., 0.5 mole, sec-butyl bromide, 70g., 0.5 mole in ether, 300 ml) was added dropwise to a stirred, cooled solution of diethyl chlorophosphite (70g., 0.45 mole) in ether (200 ml.). The rate of the addition was adjusted to keep the temperature of the reaction mixture at −60° C. When the addition was complete the solution was allowed to warm slowly to room temperature and stirred at this temperature for 1 hour. A solution of 5% ammonium chloride (250 ml.) was added and the mixture stirred for 45 minutes. The ether layer was separated and the aqueous layer was extracted four times with methylene dichloride. The organic layers were combined and dried ($MgSO_4$). The solvent was removed and the residue was distilled under reduced pressure to give ethyl sec-butylphosphinite bp. 58°–60°/0.4 mm as a colourless liquid (yield 55g., 81%).

A solution of ethyl sec-butylphosphinite (25g., 0.17 mole) in tetrahydrofuran (50 ml.) was added dropwise to a cooled solution of iso-butyl magnesium bromide (0.4 mole) in tetrahydrofuran (150 ml.). The mixture was then heated under reflux for 18 hours. The mixture was then cooled, hydrolysed with 2N $H_2SO_4$, and extracted with methylene dichloride. The combined extracts were washed with $NaHCO_3$ solution and then dried ($MgSO_4$). The solvent was removed by distillation and the residue was distilled under reduced pressure to give isobutyl sec-butyl-phosphine oxide bp. 81°–3°/0.03 0.03 mm as a colourless liquid (yield 20g., 72%).

Chlorine gas was slowly bubbled into a solution of the phosphine oxide (20g) in carbon tetrachloride (100 ml.) maintained at 9° C until the colour of the solution became pale greenish yellow. The solvent was removed and the residue was distilled under reduced pressure to give iso-butyl sec-butyl phosphinyl chloride bp. 81°–2°/.02 mm as a colourless liquid (yield 21g., 90%).

Part B

Iso-butyl sec-butyl phosphinyl chloride prepared as in Part A and n-heptyl magnesium bromide were allowed to react together as in Preparative Example A to give iso-butyl sec-butyl n-heptyl phosphine oxide bp. 123°–5°/0.004 mm.

Other compounds listed in the Table and referred to hereinafter by name may be prepared by analogous procedures.

Compositions according to the invention are illustrated by the following Examples.

EXAMPLE 1

After Shave Lotion

An after shave lotion was prepared according to the following recipe by dissolution of the ingredients in the liquid and cooling and filtering:
- Denatured Ethanol: 75%
- Diethylphthalate: 1.0%
- Propylene Glycol: 1.0%
- Lactic Acid: 1.0%
- Perfume: 3.0%
- Water: to 100%

Into separate samples of the base lotion were added 0.3% by weight based on the weight of the sample iso-butyl-sec-butyl-n-heptyl phosphine oxide and sec-butyl-n-heptyl-isopropyl phosphine oxide.

When the final solutions were applied to the face a clearly noticeable cooling effect became apparent after a short interval of time.

EXAMPLE 2

Toilet Water

A toilet water was prepared according to the following recipe:
- Denatured Ethanol: 75.0%
- Perfume: 5.0%
- Water: to 100%

To the recipe was added 0.3%, based on the total composition, of di-sec-butyl-n-hexyl-isopropyl phosphine oxide.

As with the after shave lotion, a cooling effect was clearly noticeable on the skin well after the termination of any cooling effect attributable to the evaporation of the alcoholic carrier.

EXAMPLE 3

Eye Lotion

An eye lotion was prepared containing the following ingredients:
- Witch Hazel: 12.95%
- Boric Acid: 2.00%
- Sodium Borate: 0.50%
- Allantoin: 0.05%
- Salicylic Acid: 0.025%
- Chlorobutol: 0.02%
- Zinc Sulphate: 0.004%
- Water: to 100%

To the formulation was added 0.005%, based on the total composition of di-isopentyl-sec-butyl phosphine oxide. When used to bathe the eyes a cool fresh sensation is apparent on the eyeball and eyelids.

EXAMPLE 4

Antiseptic Ointment

An ointment was prepared according to the following formulation:
- Cetyltrimethyl ammonium bromide: 4.0%
- Cetyl Alcohol: 6.0%
- Stearyl Alcohol: 6.0%
- White Paraffin: 14.0%
- Mineral Oil: 21.0%
- Water: to 100%

The ingredients were mixed, warmed to 40° C and emulsified in a high speed blender. Added to the mixture during blending was 0.5% of n-hexyl-isopentylisopropyl phosphine oxide.

The final ointment when applied to the skin gave rise to a cooling effect.

EXAMPLE 5

Antipruritic Ointment

The following ingredients were warmed together to form a homogenous melt:
- Methyl salicylate: 50.0%
- White Beeswax: 25.0%
- Anhydrous lanolin: 25.0%

To the melt was added 0.5% of di-sec-butyl-n-octyl phosphine oxide and the mixture then allowed to solidify. A soft ointment resulted having a soothing effect on the skin accompanied by a cooling effect.

EXAMPLE 6

Cleansing Tissue

A cleansing liquid was prepared having the formulation:
- Triethanolamine Lauryl sulphate: 1.0%
- Glycerol: 2.0%
- Perfume: .95%
- Water: to 100%

To this liquid was added 1.0% of di-isopentyl-n-pentyl phosphine oxide. A paper tissue was then soaked in the liquid.

When the impregnated tissue was used to wipe the skin a fresh cool sensation developed on the skin after a short interval.

EXAMPLE 7

Cigarette Tobacco

A proprietary brand of cigarette tobacco was sprayed with an ethanolic solution of sec-butyl-n-hexyl-isopropyl phosphine oxide and was rolled into cigarettes each containing approximately 50 micrograms of active compound. Smoking the impregnated cigarettes produced a cool effect in the mouth characteristic of mentholated cigarettes but without any attendant odour other than that normally associated with tobacco.

Impregnation of the filter tip of a proprietary brand of tipped cigarette with 0.05 mg. of sec-butyl-n-hexyl-isopropyl phosphine oxide produced a similar effect.

EXAMPLE 8

Toothpaste

The following ingredients were mixed in a blender:
- Dicalcium phosphate: 48.0%
- Sodium lauryl sulphate: 2.5%
- Glycerol: 24.8%
- Sodium carboxymethyl cellulose: 2.0%
- Citrus flavourant: 1.0%
- Sodium saccharin: 0.5%
- Water: to 100%

Shortly before completion of the blending operation 0.1% by weight of n-hexyl-isopentyl-isopropyl phosphine oxide was added to the blender.

When applied as a toothpaste a pleasant cooling effect is noticed in the mouth.

EXAMPLE 9

Aerosol Shaving Soap

An aerosol shaving soap composition was formulated according to the following recipe:
- Stearic acid: 6.3%
- Lauric acid: 2.7%

Triethanolamine: 4.6%
Sodium carboxymethyl cellulose: 0.1%
Sorbitol: 5.0%
Water: to 100%
Perfume: 0.5%

The composition was prepared by fusing the acids in water, adding the triethanolamine, cooling and adding the other constituents. To the mixture was then added 0.1% of n-hexyl-isopropyl-cyclopentyl phosphine oxide. The composition was then packaged in an aerosol dispenser under pressure of a butane propellant.

EXAMPLE 10

Deodorant Composition

A deodorant composition suitable for formulation and dispensing as an aerosol under pressure of a suitable propellant was formulated according to the following recipe:
Denatured ethanol: 96.9%
Hexachlorophene: 2.0%
Isopropyl myristate: 1.0%
Perfume: 0.1%

To the composition was added 1% by weight of n-heptyl-isopropyl-cyclopentyl phosphine oxide. Application of the final composition gave rise to a definite cooling sensation on the skin.

EXAMPLE 11

Hair Shampoo

Sodium lauryl ether sulphate, 10g., was dispersed in 90g. water in a high speed mill. To the dispersion was added 1.0% by weight of n-hexyl-isobutyl-isopentyl phosphine oxide. When the hair is washed using the shampoo a fresh, cool sensation is noticed on the scalp.

EXAMPLE 12

Solid Cologne

A solid cologne was formulated according to the following recipe:
Denatured ethanol: 74.5%
Propylene Glycol: 3.0%
Sodium Stearate: 5.0%
Perfume: 5.0%
Water: to 100%

The sodium stearate was dissolved by stirring in a warm mixture of the ethanol, propylene glycol and water. To the solution was added the perfume and 1.0% of n-hexyl-isobutyl-cyclopentyl phosphine oxide and the mixture then allowed to solidify into a waxy cake.

When applied to the forehead a distinct cooling effect is noticeable.

EXAMPLE 13

Mouthwash

A concentrated mouthwash composition was prepared according to the following recipe:
Ethanol: 3.0%
Borax: 2.0%
Sodium Bicarbonate: 1.0%
Glycerol: 10.0%
Flavourant: 0.4%
Thymol: 0.03%
Water: to 100.

To the composition was added 0.1% of n-heptyl-isopropyl-isopentyl phosphine oxide.

When diluted with approximately 10 times its own volume of water and used to rinse the mouth a cooling effect is obtained in the mouth.

EXAMPLE 14

Soft Drink

A soft drink concentrate was prepared from the following recipe:
Pure orange juice 60%
Sucrose: 10%
Saccharin: 0.2%
Orange flavouring: 0.1%
Citric acid: 0.2%
Sulphur dioxide: trace amount
Water: to 100%

To the concentrate was added 0.01% of diisobutyl-n-hexyl phosphine oxide.

The concentrate was diluted with water and tasted. An orange flavour having a pleasantly cool after-effect was obtained.

EXAMPLE 15

Boiled Sweet 99.5% sucrose and 0.5% citric acid were carefully fused together in the presence of a trace of water. Just before casting the melt onto a chilled plate 0.01% of n-pentyl-isobutyl-sec-butyl phosphine oxide was rapidly stirred in. The melt was then cast. A boiled sweet resulted having a marked cooling effect on the mouth.

EXAMPLE 16

Indigestion Tablet

The following ingredients were ground together:
Magnesium carbonate: 49.5%
Sorbitol: 49.4%
Saccharin: 0.1%
Talc: 1.0%

Added to the mixture during grinding was 0.1% of di-sec-butyl-n-hexyl phosphine oxide. After mixing the mixture was pressed into 0.5 g. tablets.

Taken by mouth and swallowed the tablets produced, after a short interval of time, a noticeable cooling effect in the stomach.

EXAMPLE 17

Hydrophilic Ointment

A hydrophilic ointment was prepared having the following formulation:
Propylene Glycol: 12%
1-Octadecanol: 25%
White soft paraffin: 25%
Sodium lauryl sulphate: 1%
Water: to 100%

The sodium lauryl sulphate was added to the water and heated to 60° C. The paraffin was melted by heating to 60° C and was then added to the sodium lauryl sulphate mixture with stirring. Propylene glycol and 1-octadecanol were then added to this mixture.

To the resultant mixture was added 1.5% of n-hexyl-isobutyl-sec.-butyl phosphine oxide. The final ointment when applied to the skin gave rise to a marked cooling effect.

EXAMPLE 18

Liniment

A liniment was prepared according to the following formulation:
Methyl salicylate: 25%
Eucalyptus Oil: 10%
Arachis Oil: to 100%

To the composition was added 1.5% of isobutyl-sec.-butyl-n-heptyl phosphine oxide.

When the final composition was applied to the skin a clearly noticeable cooling effect became apparent after a short interval of time.

EXAMPLE 19

Toothpick

The tip of a wooden toothpick was impregnated with an alcoholic solution containing n-hexyl-isoamyl-t.-butyl phosphine oxide in an amount sufficient to deposit on the toothpick 0.03 mg. of the compound. The toothpick was then dried.

When placed against the tongue a cool sensation is noticed after a short period of time.

The above Examples illustrate the range of compounds and the range of compositions included in the invention. However, they are not to be taken as limiting the scope of the invention in any way. Other compounds within the general formula will be equally suitable for use in the compositions of Examples 1–19 and the physiological effect obtained with the compounds of the invention will recommend their use in a wide variety of other compositions where the cooling effect will be of value.

Also provided in accordance with the present invention is a group of novel phosphine oxides having utility as agents for stimulating the cold receptors of the nervous system of the body and useful in ingestible, toilet and cosmetic compositions, and in tobacco and tobacco-containing manufactures, these being phosphine oxides of the formula:

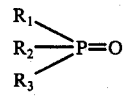

where $R_1$ is a straight chain alkyl group of from 4–9, preferably 5–8, carbon atoms inclusive, $R_2$ is a branched chain alkyl group of from 3–8, preferably 3–5, carbon atoms inclusive and preferably having branching at an α- or β-position relative to the phosphorus atom, and $R_3$ is an alkyl or cycloalkyl group of from 4–8 carbon atoms inclusive, preferably either a branched chain alkyl group containing from 4–5 carbon atoms or cyclopentyl, $R_1$, $R_2$ and $R_3$ together providing a total of from 13–17 carbon atoms, preferably 13–16.

Particularly important and preferred novel compounds within this selected group are:

n-hexyl-isopropyl-cyclopentyl phosphine oxide;
n-heptyl-isopropyl-cyclopentyl phosphine oxide;
isobutyl-n-hexyl-cyclopentyl phosphine oxide;
isobutyl-sec.-butyl-n-hexyl phosphine oxide;
isobutyl-sec.-butyl-n-heptyl phosphine oxide;
isobutyl-n-hexyl-isopentyl phosphine oxide;
t.butyl-n-hexyl-isopentyl phosphine oxide;
sec.-butyl-n-heptyl-isopropyl phosphine oxide;
sec.-butyl-n-octyl-isopropyl phosphine oxide;
isobutyl-sec.-butyl-n-octyl phosphine oxide;
di-sec.-butyl-n-octyl phosphine oxide;
sec.-butyl-n-hexyl-isopropyl phosphine oxide; and
n-hexyl-isopentyl-isopropyl phosphine oxide.

We claim:

1. In a manufactured consumer product for application to or consumption by the human body, said product comprising (a) a topically administrable or orally ingestible carrier and one or more of the following: a flavourant, colourant, odourant, antiseptic, antacid or analgesic, and (b) a compound capable of stimulating the cold receptors of the nervous system in the surface tissues of the body when brought into contact therewith by application or consumption of the said product, the improvement which comprises using as the cold receptor stimulating compound, an effective amount of a cold receptor stimulating phosphine oxide of the formula

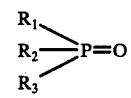

where
$R_1$ is a straight chain alkyl group having from 4–8 carbon atoms inclusive;
$R_2$ is a branched chain alkyl group having from 3–5 carbon atoms inclusive; and
$R_3$ is an alkyl group having from 3–6 carbon atoms inclusive or cyclopentyl;
$R_1$, $R_2$ and $R_3$ together providing a total of from 13–16 carbon atoms.

2. A product according to claim 1, wherein the cold receptor stimulant is of the formula defineld, where $R_1$ is a straight chain alkyl group of from 5–8 carbon atoms inclusive, $R_2$ is selected from isopropyl, sec.-butyl, isobutyl and isopentyl, and $R_3$ is selected from branched chain alkyl groups of from 4–5 carbon atoms inclusive and cyclopentyl, $R_1$, $R_2$ and $R_3$ together providing a total of from 13–16 carbon atoms.

3. A product according to claim 1, wherein the cold receptor stimulant is selected from:
n-hexyl-isopropyl-cyclopentyl phosphine oxide;
n-heptyl-isopropyl-cyclopentyl phosphine oxide;
isobutyl-n-hexyl-cyclopentyl phosphine oxide;
isobutyl-sec.-butyl-n-hexyl phosphine oxide;
isobutyl-sec.-butyl-n-heptyl phosphine oxide;
isobutyl-n-hexyl-isopentyl phosphine oxide;
t.butyl-n-hexyl-isopentyl phosphine oxide;
sec.butyl-n-heptyl-isopropyl phosphine oxide;
sec.butyl-n-octyl-isopropyl phosphine oxide;
isobutyl-sec.-butyl-n-octyl phosphine oxide;
di-sec.-butyl-n-octyl phosphine oxide;
sec.butyl-n-hexyl-isopropyl phosphine oxide; and
n-hexyl-isopentyl-isopropyl phosphine oxide.

4. A product according to claim 1, which is a toilet lotion comprising an aqueous, alcoholic or aqueous-alcoholic base; an antiseptic, perfuming agent, colorant or mixture thereof; and said cold receptor stimulating compound.

5. A product according to claim 1, which is a cosmetic preparation comprising an oil-in-water emulsion cosmetic base; an antiseptic, perfuming agent, colorant or mixture thereof; and said cold receptor stimulating compound.

6. A product according to claim 1, which is a toilet soap, into which there is incorporated an effective amount of said cold receptor stimulating compound.

7. A product according to claim 1, which is a shaving soap, foam or cream into which there is incorporated an effective amount of said cold receptor stimulating compound.

8. A product according to claim 1, which is an edible or potable preparation comprising an edible or potable base; a flavorant on colorant or a mixture thereof, and an effective amount of said cold receptor stimulating compound.

9. A product according to claim 1, which is a chewing gum into which there is incorporated an effective amount of said cold receptor stimulating compound.

10. A method of stimulating the cold receptors of the nervous system of the human body which comprises applying thereto an effective amount of a cold receptor stimulating compound of the formula defined in claim 1.

* * * * *